United States Patent
Wang

(10) Patent No.: US 6,759,197 B2
(45) Date of Patent: Jul. 6, 2004

(54) MICROCHIP ARRAYS OF REGULATORY GENES

(75) Inventor: Eugenia Wang, Prospect, KY (US)

(73) Assignee: Sir Mortimer B. Davis -- Jewish General Hospital, Montreal (CA)

( * ) Notice: Subject to any disclaimer, the term of this patent is extended or adjusted under 35 U.S.C. 154(b) by 216 days.

(21) Appl. No.: 09/821,203

(22) Filed: Mar. 29, 2001

(65) Prior Publication Data

US 2002/0012932 A1 Jan. 31, 2002

Related U.S. Application Data

(60) Provisional application No. 60/193,888, filed on Mar. 31, 2000.

(51) Int. Cl.$^7$ .......................... C12Q 1/68; C07H 21/02; C07H 21/04
(52) U.S. Cl. .......................... 435/6; 536/23.1; 536/24.3
(58) Field of Search .............................. 435/6; 536/23.1, 536/24.3

(56) References Cited

U.S. PATENT DOCUMENTS

| | | | |
|---|---|---|---|
| 5,474,796 A | * 12/1995 | Brennan | |
| 5,605,662 A | * 2/1997 | Heller et al. | |
| 5,880,261 A | * 3/1999 | Waeber et al. | 530/350 |
| 6,329,140 B1 | * 12/2001 | Lockhart et al. | |
| 6,444,421 B1 | * 9/2002 | Chung | 435/6 |
| 6,444,463 B1 | * 9/2002 | Tapscott | 435/325 |
| 6,524,800 B2 | * 2/2003 | Lockhart et al. | |
| 6,620,914 B1 | * 9/2003 | Waeber et al. | 530/358 |
| 6,653,102 B2 | * 11/2003 | Roch et al. | 435/69.1 |

FOREIGN PATENT DOCUMENTS

| WO | WO9525116 | * 9/1995 |
|---|---|---|
| WO | WO9535505 | * 12/1995 |

OTHER PUBLICATIONS

DeRisi et al., Nature Genetics 14 (4) : 457–460 (Dec. 1996).*
Lockhart et al., Nature 405 : 827–836 (Jun. 15, 2000).*
Heller et al., PNAS 94 : 2150–2155 (1997).*
Schena et al., PNAS 93 : 10614–10619 (1996).*
Bodescot & Brison, "Characterization of new human c–myc mRNA species produced by alternative splicing," *Gene* 174:115–120 (1996).
Bowtell, "Options available—from start to finish—for obtaining expression data by microarry," *Nature Genetics* Supplement 21:25–32 (1999).
Constantine & Harrington, "Use of GeneChip high–density oligonucleotide arrays for gene expression monitoring," *Life Science News* 1:11–13 (1998).
Dang, "c–Myc target genes involved in cell growth, apoptosis, and metabolism," *Mol. Cell Biol.* 19:1–11 (1999).
Eilers, "Control of cell proliferation by Myc family genes," *Mol. Cells* 9:1–6 (1999).
Facchini & Penn, "The molecual role of Myc in growth and transformation: recent discoveries lead to new insights," *FASEB Journal* 12:633–651 (1998).
Lee, et al., "Gene expression profile of aging and its retardation by caloric restriction," *Science* 285:1390–1393 (1999).
Ramsay, "DNA chips: State of the Art," *Nature Biotechnology* 16:40–44 (1998).
Wang, et al., "Large–scale identidication, mapping, and genotyping of single–nucleotide polymorphisms in the human genome," *Science* 280:1077–1082 (1998).
Zhang, et al., "Gene expression profiles in normal and cancer cells," *Science* 276:1268–1272 (1997).

* cited by examiner

*Primary Examiner*—Ethan Whisenant
(74) *Attorney, Agent, or Firm*—Patrea L. Pabst, Esq.

(57) ABSTRACT

Microarray technology is a fast-growing field of biomedical research, aiming to investigate changes in molecular features of hundreds of genes. The multiple parallel processing of information generated from matrices of huge numbers of loci on a solid substrate has allowed the gathering of gene signatures defining specific biological states. A new approach has been developed to facilitate this process wherein genes of the same regulatory modality are selected. The transcriptional regulation of these genes is related to the same control element, the E-box, defined by the sequence CACGTG. PCR products of selected regions of all known genes either binding to this sequence or whose expression is dependent on this binding, as well as genes interacting with E-box-binding genes and control genes, are arrayed on a nylon membrane or other appropriate microchip susbstrate, which is then used as an E-box-specific microarray. The transcriptionally regulated profile of E-box-related genes specific to a given cultured cell sample is then determined by unique labeled cDNAs probes produced from RNAs isolated from the culture of interest.

9 Claims, 6 Drawing Sheets

|   | 1 | 2 | 3 | 4 | 5 |
|---|---|---|---|---|---|
| a | HeLa DNA* | Phos. A2 | HPRT1 | GAPDH | HeLa DNA* |
| b | HeLa DNA* | A-tubulin | HLA-C | B-actin | Aldolase C |
| c | Salmon DNA | RPS9 | UBC | RPL-13A | Salmon DNA |
| d | ID3 | MrDb | Mad1 | c-Myc,exon2-3 | TFII-I |
| e | MBP-1 | MM-1 | KIAA0801 | Max | c-Myc,exon1 |
| f | DIP1 | Nm23-H2S | LEF1 | MYCL1 | ID2 |
| g | ODC1 | PTMA | MYCL2 | HTF4 | HOX-B6 |
| h | Mxi1 | RBMS1 | Cdc25A | ZEP161 | ABF1 |
| i | USF2 | TCF3 | ZEB | EST,Mad/Mxi1 | TCF4 |
| j | NeuroD | TFEB | MITF-A | MNT(ROX) | Pam |
| k | ID4 | RBMS2 | ATOH1 | MYF6 | N-Myc |
| l | HeLa DNA* | Salmon DNA | Lambda DNA | Salmon DNA | HeLa DNA* |
| m | HATH1 | MYF4 | NHLH1 | MYF-5 | YY1 |
| n | USF1 | hMad4 | TFECL | AP-4 | Est, Mad4 |
| o | TWIST | MyoD1 | Lambda DNA | Lambda DNA | 2xSSC |

\* -HeLa DNA= HeLa cell genomic DNA; positions 1a, 1b, 1l, and 5a contain 100ng/μl, position 5l contains 450 ng/μl HeLa cell genomic DNA

FIG. 1

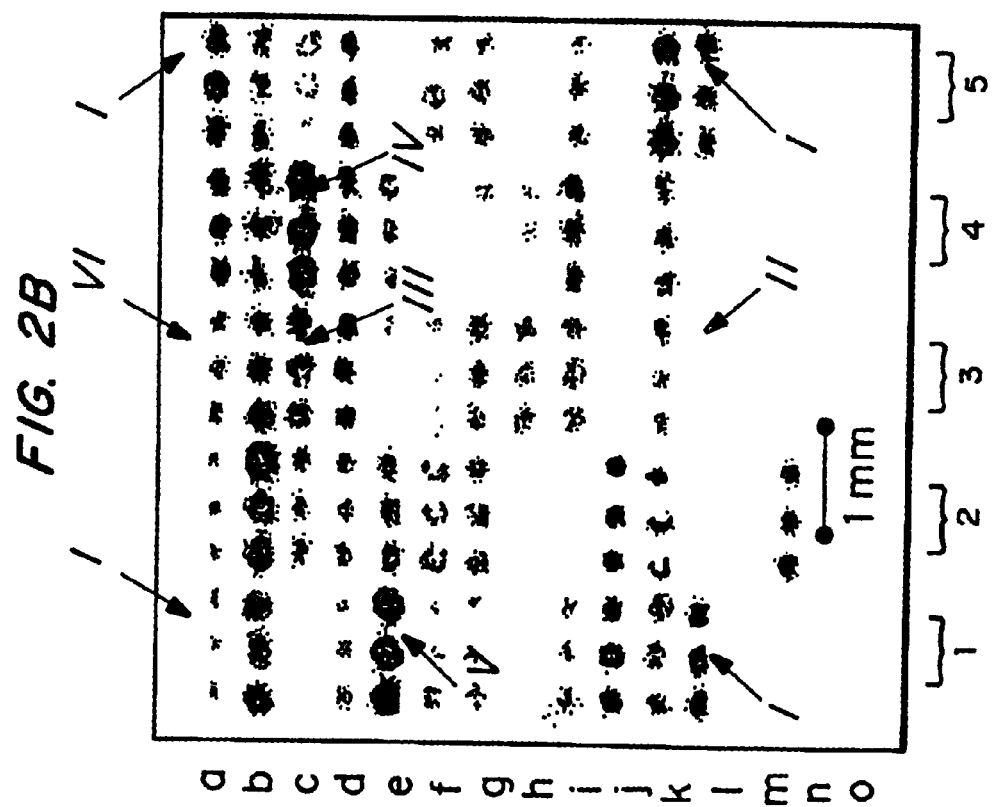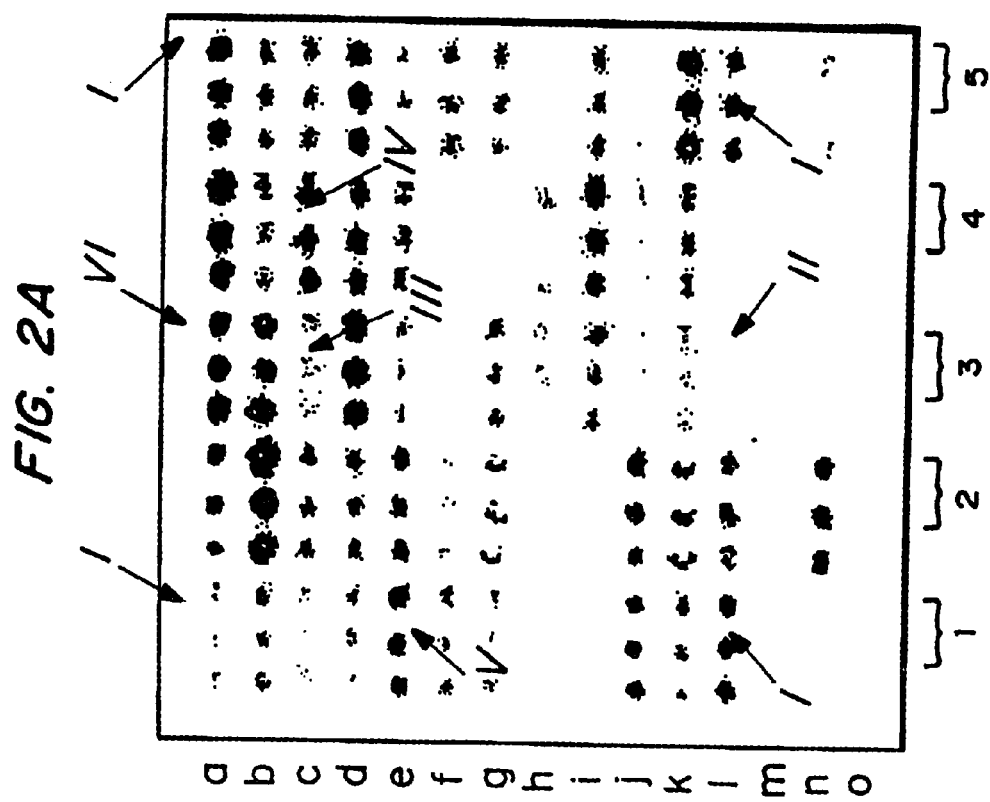

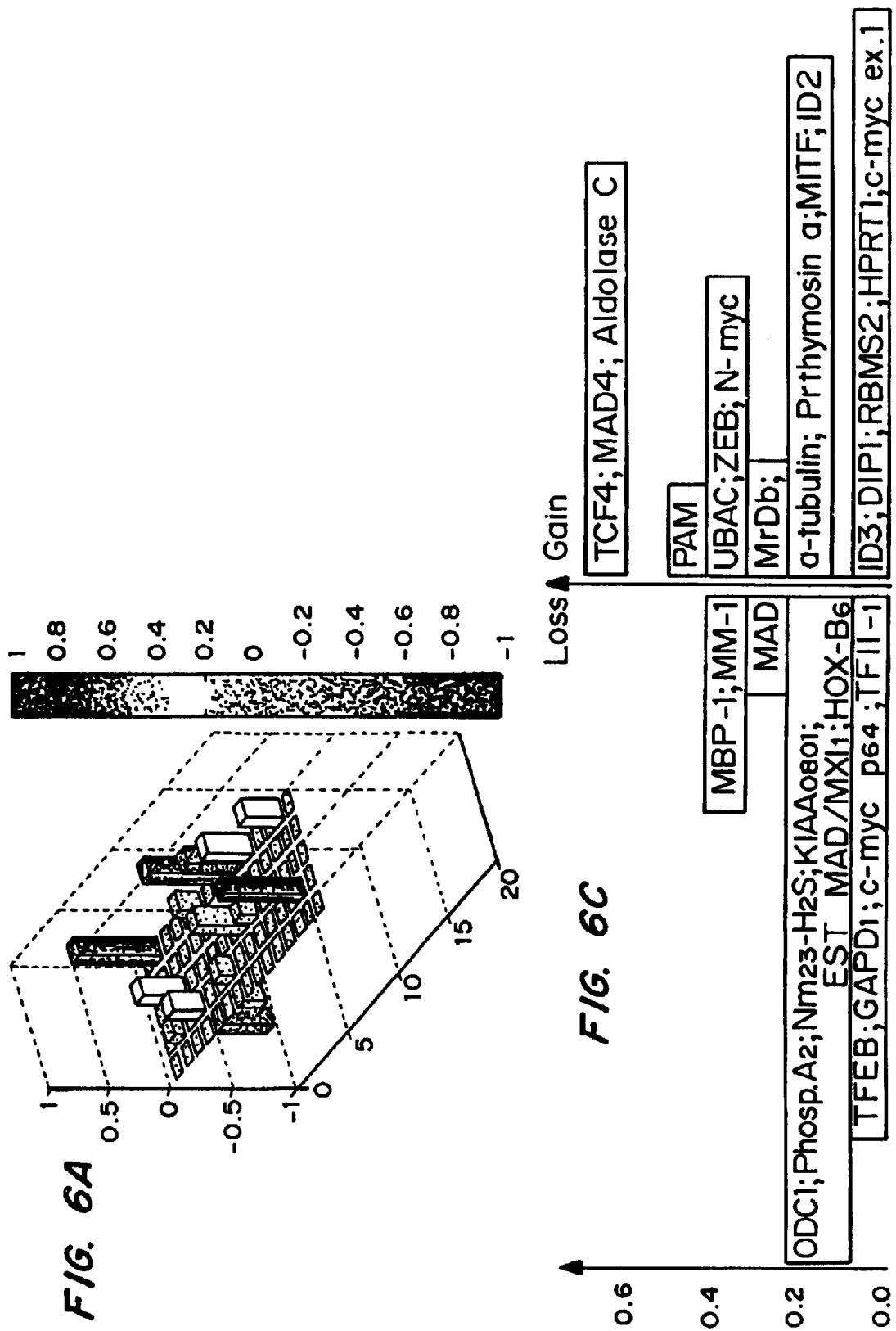

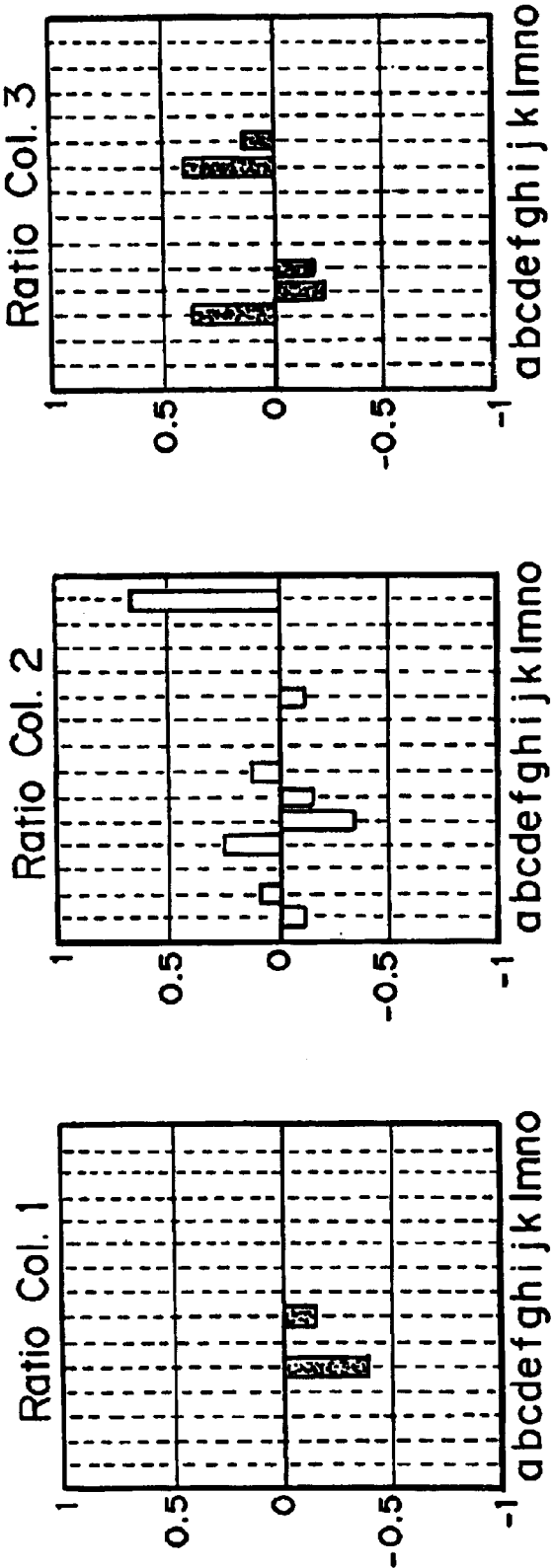
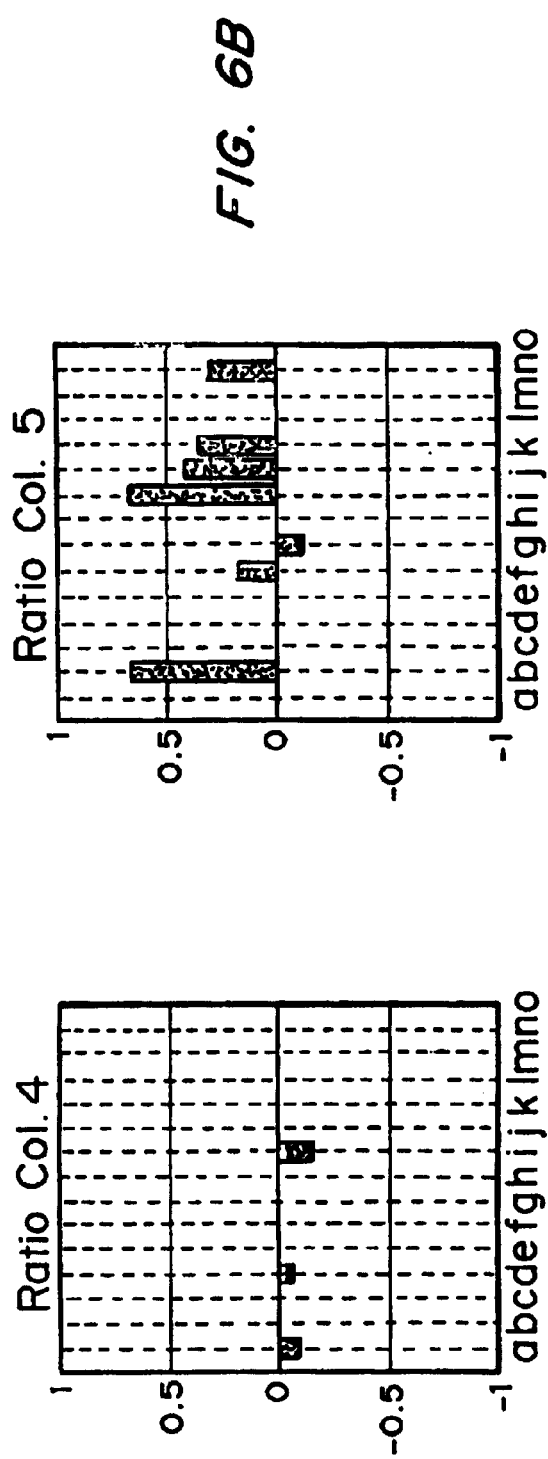
FIG. 6B

MICROCHIP ARRAYS OF REGULATORY GENES

This application claims priority to U.S. Ser. No. 60/193,888 filed Mar. 31, 2000.

The United States government has certain rights in this invention by virtue of grants to Eugenia Wang from the National Institute on Aging (AG09278) and from the Defense Advance Research Project Agency (DARPA) of the Department of Defense of the United States of America.

BACKGROUND OF THE INVENTION

With the advent of the Human Genome Project, one is confronted with voluminous information demonstrating that biological systems may be controlled by hundreds of genes working in concert. A single glance at the ever-increasing number of genes involved in signal transduction makes one wonder just how many genes are needed-to choreograph the symphonic dance of implementing a signal, from the receptor-ligand binding to the nuclear response of transcriptional activation. During the 1980's and early 1990's, biologists were busy dissecting single genes' functions from the reductionist point of view. This approach, while thorough in its exact methodological analysis of genetic impact, lacks the expanded vision of how each particular single gene functions in the context of many sister genes or partners, to accomplish a biological task. Thus, it is not surprising that the technology of high-throughput gene screening is emerging rapidly, in the attempt to identify tens or hundreds of genes whose changes, viewed in composite genetic signatures, define a particular physiological state. This gene signature approach, complemented by single gene analysis, provides a vertical, in-depth analysis of an individual gene's function, as well as the comprehensive picture of the pattern of gene expression in which the particular gene functions. The notion of genetic signature can be further generalized to address the question of inter-individual variance, by comparing individuals from cohorts of hundreds or thousands.

The unfathomable task of comparing several dozens of single nucleotide polymorphisms (SnP) in a hundred people can now be approached easily by DNA biochip technology (Wang, et al. Science 280:1077–1082 (1998)). For example, a p53 DNA chip is used popularly for the identification and gene screening of unique cancer risks, to discover new SnPs as well as screening known SnPs. Either task needs a fast, multiplex approach requiring data entry on the scale of hundreds and thousands, a demand that can only be met by high-throughput technology. The presently available microarray biochip technology is certainly the method of choice to solve the problem of complexity, and the previously impossible task of defining a genetic signature for a unique person in a cohort with accuracy and speed that are impossible by the conventional diagnostic approach. Therefore, from bench-side researchers to bedside physicians, there is intense interest in the technology of microarray analysis, for screening or identifying tens or hundreds of genes related to disease or normal states of a given person or biological system.

cDNA and oligonucleotide microarrays are becoming an increasingly powerful technique for investigating gene expression patterns. In spite of the fast progress in this field, some limitations of the technique persist. One of the major obstacles is the requirement for a large amount of mRNA. Another problem with existing microarray systems is data mining; while information on expression of tens of thousands genes is absolutely vital to estimate the functions of new genes, in some instances a researcher is interested in the expression profile of only a subset of genes, in many physiological conditions.

It is an object of the present invention to provide a method and materials for the rapid analysis of genetic information based on a common regulatory feature.

It is a further object of the present invention to provide a method and materials for sensitive and quick analysis of genetic information present in very small quantities.

SUMMARY OF THE INVENTION

Microarray technology is a fast-growing field of biomedical research, aiming to investigate changes in molecular features of hundreds of genes. The multiple parallel processing of information generated from matrices of huge numbers of loci on a solid substrate has allowed the gathering of gene signatures defining specific biological states. A new approach has been developed to facilitate this process wherein genes of the same regulatory modality are selected. The transcriptional regulation of these genes is related to the same control element, the E-box, defined by the sequence CACGTG. PCR products of selected regions of all known genes either binding to this sequence or whose expression is dependent on this binding, as well as genes interacting with E-box-binding genes and control genes, are arrayed on a nylon membrane or other appropriate microchip susbstrate, which is then used as an E-box-specific microarray. The transcriptionally regulated profile of E-box-related genes specific to a given cultured cell sample is then determined by unique labeled cDNAs probes produced from RNAs isolated from the culture of interest.

The production of E-box microarrays provides an approach to custom-adapt the gene screening task to analyze a subgroup of gene expressions controlled by the same molecular modality. E-box binding-related genes represent a specific group of basic helix-loop-helix/leucine zipper transcription factors, recognizing the core-binding site CACGTG. They play important roles in regulation of basic cellular functions, like proliferation and apoptosis (c-Myc) or tissue-specific differentiation (Myod). As demonstrated by the example, careful selection of genes for the microarray allowed extraction of E-box gene specific signatures of HeLa cells and normal human lymphocytes. The significant differences in expression of 3–6 genes out of 61 are already much more manageable than can be detected from ordinary microarrays with massive numbers of genes, in the hundreds or thousands.

BRIEF DESCRIPTION OF THE DRAWINGS

FIG. 1 depicts cDNA microarray hybridization for evaluation of E-box binding-related gene expression. The matrix position, with each gene's abbreviation, is written underneath each locus of three repeats of dots with identical amounts deposited; the X-coordinates denote the number 1, 2, 3, 4, and 5 positions, and Y-coordinates denote the "a" through "o" positions. The matrix location for each gene triplet is then identified as X,Y coordinates. For example, 5k denotes the position of N-Myc, and 3d denotes of the position of Mad. The same coordinates are also included in Table 2.

FIGS. 2A and 2B shows the expression profiles of E-box binding-related gene expressions in Hela cells. FIG. 2A—total RNA was labeled with digoxigenin in RT reaction with gene specific primers; FIG. 2B—mRNA was labeled with digoxigenin in RT reaction with oligo(dT) primers. Arrows within the matrix show positions of: I—Hela DNA (positive control); II—lambda DNA (negative control); III—UBC; IV—RPL-13A; V—MBP-1; VI—HPRT1. The distance between dots can be measured by the bar of 1 mm.

FIGS. 6A, 6B and 6C are pairwise comparisons of E-box gene expression in Hela cells and human lymphocytes. Two independent hybridizations are averaged for each type of cell. FIG. 6A—Three-dimensional, and FIG. 6B—two-dimensional, representations of differences in gene expression. Each panel corresponds to one column in FIG. 5A, and each bar represents an individual gene. FIG. 6C—Distribution of genes with common gain (red) or loss (blue) of expression in dependence on relative ratio value. The relative fold ratio between samples S1 and S2 is computed as $$R_{DM}(S_1, S_2) = \frac{(S_2 - S_1)}{\max(S_1, S_2)}$$

Figure 3:
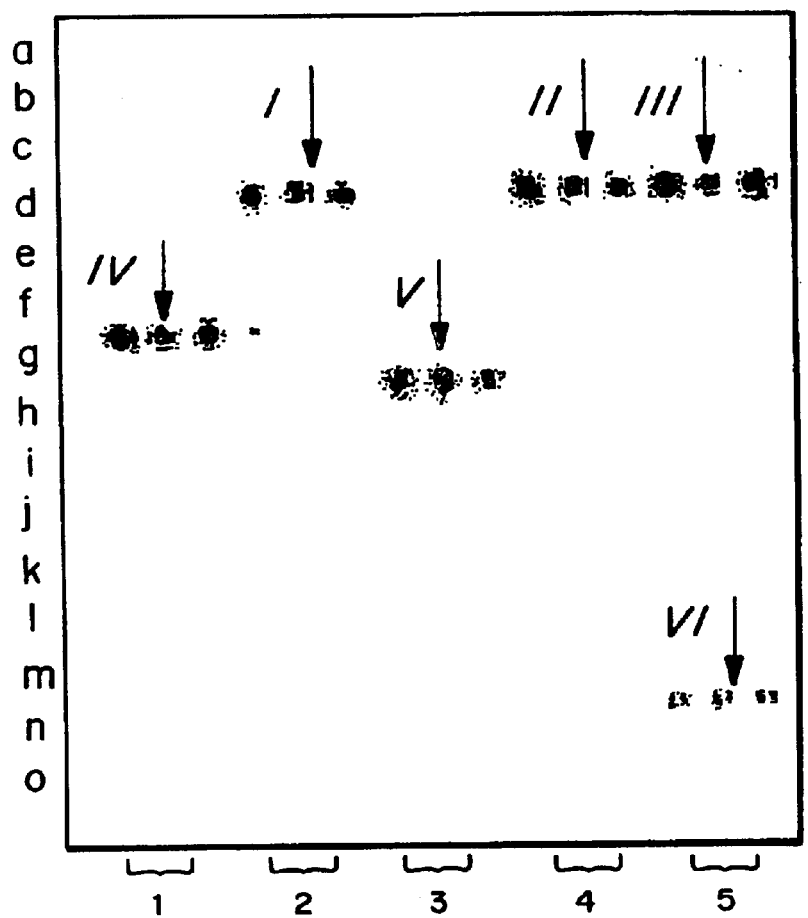
FIG. 3 depicts hybridization of products of multiplex PCR with 5 pair of primers with cDNA microarray. Arrows within the matrix point to: I—Mrdb; II—c-Myc p64; III—TFII-1; IV—ODC1; V—cdc25A; VI—Hela genomic DNA.

which yields a value in the range of [−1,+1]. Positive values correspond to up-regulation, and negative values correspond to down-regulation, of genes in sample S2. The relative fold ratio has a similar meaning to that of conventional fold ratio, except that the value is normalized and symmetric, with clear physical interpretation. $R_{DM}(S_1,S_2)=\pm 0.5$ corresponds to a two-fold up- or down-regulation in normalizing the two samples; a set of housekeeping genes of relatively constant expression levels were selected as controls, and linear normalization was applied.

DETAILED DESCRIPTION OF THE INVENTION

E-box Regulatory Genes

The production of E-box microarrays provides an approach to custom-adapt the gene screening task to analyze a subgroup of gene expressions controlled by the same molecular modality. E-box binding-related genes represent a specific group of basic helix-loop-helix/leucine zipper transcription factors, recognizing the core-binding site CACGTG. As used herein, E-box genes refer to all genes having the E-box in their promoter region, as well as E-box binding and interacting genes. They play important roles in regulation of basic cellular functions, like proliferation and apoptosis (c-Myc) or tissue-specific differentiation (Myod). As demonstrated by the example, careful selection of genes for the microarray allowed extraction of E-box gene specific signatures of HeLa cells and normal human lymphocytes. The significant differences in expression of 3–6 genes out of 61 are already much more manageable than can be detected from ordinary microarrays with massive numbers of genes, in the hundreds or thousands. For example, in SAGA analysis of 45,000 genes, it was found that about only 1% are differentially expressed in normal and cancerous human cells (Zhang, et al., Science 276, 1268–1272 (1997)). A similar estimation resulted from analysis of expression profiles in young and old mice; expressions of only 1.8% of about 6,000 genes are changed more than 2-fold (Lee, et al., Science 285, 1390–1393 (1999)).

The best-known representative of E-box-binding genes is c-Myc, whose transactivating activity plays crucial roles in the regulation of cell cycle, proliferation and apoptosis (Eilers, Mol. Cells 9, 1–6 (1999); Dang, C. V. Mol. Cell Biol. 19, 1–11 (1999); Facchini and Penn, FASEB J. 12, 633–651 (1998)). For this reason, genes interacting with or regulating expression for c-Myc, as well as some target genes whose expression is E-box-binding-dependent, are included in this microarray. Representative E-box genes are shown in Table 2.

Housekeeping Genes

Housekeeping genes are used to normalize results of expression. These are genes that are selected based on the relatively invariable levels of expression in the system which is being examined, for example, the state such as age or a particular disease. Representative housekeeping genes are shown in Table 2. These include tyrosine 3-monooxygenase/tryptophan 5-monooxygenase activation protein, hypoxanthine phosphoribosyltransferase I (Lesh-Nyhan syndrome), Major histocompatibility complex, class I, C, Ubiquitin C, Glyceraldehyde-3-phosphate dehydrogenase, Human mRNA fragment encoding cytoplasmic actin, 60S Ribosomal protein L13A, and Aldolase C.

Probes

In the preferred embodiment, a set of primers for use in detecting changes in expression of genes include the E-box regulatory sequence, are between 480 and 700 base pairs length, have a melting point between 75 and 85° C., and include non-consensus sequence with protein coding sequence, so that there is no detectable hybridization between homologous genes, more preferably where there is no hybridization between homologous genes. Examples of homologous genes include c-myc and c-myc associated genes.

Diseases and States

The changes in expression of the E-box regulatory genes described herein can be used to assess changes associated with a particular state or disease. The association of certain E-box genes such as c-myc with cancer and neurodegeneration, and its role in apoptosis, are well established. Other genes include yy1, myc-L1, and myc-L2, which affect cells, cell components, and specific molecules, for example, cardiomysin, myotube, osteoblasts, and osteoclasts. Changes in expression of individual genes, either by turning expression on or off, or altering the amount of expression, can be used to assess changes in states such as age or diseases associated with cancer of tissues such as breast, prostate, and colon, immunological changes such as inflammation, neurodegenerative diseases, cardiovascular disorders, and musculoskeletal disorders, including disorders and diseases of bones such as osteoarthritis and osteoporosis, and muscle degeneration.

Screening

The arrays can be tested by screening with labeled probes to determine if there is expression of a particular gene in the array and how much, to thereby construct a "fingerprint" of the disease or disorder at that time, using genes present in cells or tissues obtained from one or more individuals having the disease or disorder or characterized by a particular state, such as age. The effect of a compound or composition on the disorder or disease or state can also be assessed by comparing the fingerprint obtained with control cells or tissues, and cells or tissues treated with the compound or obtained from an animal treated with the compound (or compounds, or dosage regime, or exposed to particular conditions). This is especially useful for initial screening of the effect of potential drugs, either to determine potential efficacy and/or toxicity. Those compounds which appear promising can then be further screened to determine if they can reduce or reverse the severity of the disease or disorder. Compounds to be screened can be proteins or peptides, sugars or polysaccharides, nucleic acid molecules, or synthetic molecules.

MicroChip Array Technology and Analysis
Information Resources

There are several DNA microchip technology reviews in the literature (Bowtell, D. D. L. Nature Genetics Supplement 21:25–32 (1999); Constantine, and Harrington Life Science News 1:11–13 (1998); Ramsay, G Nature Biotechnology 16:40–44 (1998)), and several good web sites detailing the apparatus and protocols used by other laboratories, nothing in the literature offers a description of a working arrangement to serve as a user-friendly guide. Table 1 lists several good web sites for highly active laboratories in DNA microchip technology, as well as several sources of robotics systems and equipment, imaging software and systems and vendors of robotic components.

The Microarrayer

A turnkey microarrayer can be purchased, with an enclosure for temperature, humidity and air quality control; a system such as the GeneMachines™ OmniGrid (San Carlos, Calif.) would be sufficient. Alternatively, to save on the cost of a robotic system, a microarrayer can be built in the laboratory. The Brown Laboratory web site, for example, gives full details for component specifications, mechanical drawings for machined parts, a list of vendors, an assembly guide, and free microarrayer software.

Operation of the Tips, XYZ Motion Control, and Computer Program

The robotic gantry of a typical printing tip microarryer is composed of 3 individual assemblies of linear robotic tables, and motors driven by 3 corresponding amplifiers which are coupled to a motion controller in the driving computer. All of this forms the appropriate 3-axis motion control system (i.e.: X, Y and Z axes) for microarraying. The three perpendicular axes allow for sampling, printing and washing with the components of the microarryer system.

Printing Substrate and Samples

In terms of a printing substrate for producing the microchips, poly-L-lysine-coated glass slides seem to work best to immobilize the printed DNA. Nylon hybridization membranes can also be used as the printing substrate, and allow for a much easier immobilization protocol, as well as better visualization if a colorimetric method is used for hybridization detection.

To contain the samples, conical 96-well microplates work well by localizing small volumes of sample in the wells. When printing many different samples, 384-well microplates are best due to their higher capacity and low storage volume and the smaller sample sizes ($\leq 10$ $\mu$l) can be used readily. During storage, sample plates should be covered with an adhesive-backed plastic seal, to prevent sample loss by evaporation.

Sample Preparation

Samples prepared for printing are loaded into 384-well microplates, 10 $\mu$l aliquots per well. These samples can be used for up to 8 to 10 printing runs, with proper storage. In printing arrays with the ArrayIt™ printing tips on the GeneMachines™ OmniGrid microarrayer, it is possible to print several thousand spots onto one chip either in one array or duplicate arrays on one chip. The printing tip delivery volume is approximately 1 nl per spot with a spot diameter of approximately 100 $\mu$m. Therefore, depending upon the surface area of the substrate being used as the chip and the number of tips used for printing, several large arrays are possible with close spacing (less than 100 um) for up to 100 chips per run. For typical experiments in this laboratory, arrays are printed in duplicate 20×20 arrays per chip with a spot spacing of 250 $\mu$m using between 20 to 30 chips per run.

To extend the lifetime of the samples, after printing, the microtiter plates are sealed with adhesive-backed plastic covers in addition to the microplate lids. Furthermore, before using the stored samples again, the microplates are centrifuged to gather any condensate in the wells, and to localize the sample fluids at the bottom of each well.

Array Analyzer/Imaging System

Depending upon the selected approach to hybridization analysis of the printed microarrays, a system fitted onto an existing microscope, a microarray scanner or confocal laser scanner may be purchased, or a confocal laser scanner may be built.

The system used to compile the digital microarray images is built around an Olympus BH-2 upright light microscope, fitted with a Sony color CCD camera, an Applied Scientific Instrumentation (Eugene, Oreg.) X-Y scanning stage, and a fiber optic ring illuminator from Edmund Scientific Co. (Barrington, N.J.). EMPIX Imaging, Inc. (Mississauga, ON) assembled the system for compiling microarray images, containing a 24 bit frame grabber; it is installed in a 450 MHz P3 PC equipped with 512 Mb RAM and a 19" SVGA monitor, where the image acquisition and system control are governed under the Windows 98 operating system by Northern Eclipse™ imaging software. A 3COM™ 10/100 Base TX network card installed in the computer links the imaging computer to a small LAN (Lynksys, Irvine, Calif.), containing a color laser printer and two other computers used for image analysis and data storage.

The size of the arrays and individual spots dictates the use of low power objectives (either 2.5X or 4X) and the X-Y scanning stage to capture the image of the entire array.

Many of our microarray experiments are done using nylon membranes (Hybond-N) as the printing substrate. Probes are labeled with DIG-dUTP in a reverse transcription reaction; target/probe hybridization is detected with anti-DIG-coupled alkaline phosphatase, and a subsequent reaction of the alkaline phosphatase with an NBT/BCIP stain/substrate. This method requires the ring illuminator to distinguish artifacts from array spots on the stained hybridization membranes. Otherwise, if poly-L-lysine coated glass slides are used as the microarray printing substrate, illumination of the microarray specimen is carried out normally.

Image Quantitation

When the microarray digital imaging routine is completed, the compiled montage can be transferred by way of the network to the computer stations devoted to image analysis and data storage. The microarray images are created as TIFF files; before quantitation can begin, the raw digital images are filtered to bear only the microarray signal data, aligned in Adobe PhotoShop™ software, and then transferred to the GeneAnalyzer microarray analysis software. GeneAnalyzer removes the background, and the reduced digital microarray images are passed through an image location routine to optimally localize the spots of the microarray image. When the GeneAnalyzer software has "grabbed" the individual spots of the reduced digital microarray image, the program can proceed to quantitate the density of the individual spots. Each spot on the microarray is then regarded as an individual signal, and its intensity serves as the foundation of the data needed to reflect the hybridization reaction. After comparison with appropriate positive and negative controls for nonspecific reactions, true signal value is subtracted from noise to produce the desired information on each hybridization reaction.

The microarray spot density data are transferred into an analysis routine in the mathematical analysis software, MATLAB, for graphical representation of all data; the density values, as well as the respective calculated values, of all digitized microarray data are tabulated in a Microsoft Excel™ spreadsheet. A full record of the progression of images, tabulated data and all graphical representations can immediately be printed to complete the microarray experiment analysis.

Labels for Probes and Detection

Microarrays typically contain at separate sites nanomolar (less than picogram) quantities of individual genes, cDNAs, or ESTs on a substrate such as a nitrocellulose or silicon plate, or photolithographically prepared glass substrate. The arrays are hybridized to cDNA probes using standard techniques with gene-specific primer mixes. The nucleic acid to be analyzed—the target—is isolated, amplified and labeled, typically with a fluorescent reporter group, radiolabel or phosphorous label probe. After the hybridization reaction is completed, the array is inserted into the scanner, where patterns of hybridization are detected. The hybridization data are collected as light emitted from the reporter groups already incorporated into the target, which is now bound to the probe array. Probes that perfectly match the target generally produce stronger signals than those that have mismatches. Since the sequence and position of each probe on the array are known, by complementarity, the identity of the target nucleic acid applied to the probe array can be determined.

There are a variety of labels that are used. cDNAs and ESTs can be detected by autoradiography or phosphorimaging ($^{32}P$). Fluorescent dyes are also used, and are commercially available from suppliers such as Clontech.

In the preferred embodiment the label is digoxigenin (DIG). This specific enzymatic labeling probe allows the end result of detecting hybridization reaction intensity by colorimetric evaluation of alkaline phosphatase-coupled antibody to DIG. The enzymatic deposit on each locus of the E-box microarray can be readily analyzed by an upright microscope attached to a CCD camera, without the problem of the long delay needed for exposure time with radioactive probes, or the photobleaching and high background reaction problem associated with the fluorescent probe approach.

TABLE 1

Informative web sites for DNA microarray technology

| DNA microarray technology web sites | URL |
| --- | --- |
| Automation and Miniaturization in Genome Analysis, Max Plank Institute for Molecular Genetics | http://www.mpimg-berlin-dahlem.mpg.de/~autom/autom.htm |
| Department of Molecular Biotechnology, University of Washington | http://chroma.mbt.washington.edu/mod_www/ |
| Functional Genomics Group, Albert Einstein College of Medicine | http://sequence.aecom.yu.edu/bioinf/funcgenomic.html |
| Genomics Group, Children's Hospital of Philadelphia | http://w95vcl.neuro.chop.edu/vcheunng |
| Laboratory of Cancer Genetics, National Human Genome Research Institute | http://www.nhgri.nih.gov/Intramural_research/Lab_cancer/ |
| Joint Genome Institute, Lawrence Livermore National Laboratory | http://llnl.gov/automation-robotics/poster.1.html |
| Pat Brown Laboratory, Stanford University | http://cmgm.stanford.edu/pbrown |
| Stanford DNA sequence and Technology Center Stanford University | http://-sequence.stanford.edu/group/techdev/ |
| Microarrayers, imaging systems and scanners | |
| Applied Scientific Instrumentation, Inc. | http://www.ASIimaging.com/ |
| Axon Instruments, Inc. | http://axon.com/GN_Genomics.html |
| Beecher Instruments | http://www.beecherinstruments.com/ |
| BioDiscovery, Inc. | http://www.biodiscovery.com/ |
| BioRobotics, Ltd. | http://www.biorobotics.com/ |
| Empix Imaging, Inc. | http://www.empix.com/ |
| GeneMachines, Genomic Instrumentation Services, Inc. | http://www.genemachines.com/ |
| General Microarray Information | http://www.microarray.org/ |
| General Scanning, Inc. | http://www.genscan.com/ |
| Genetic MicroSystems, Inc. | http://www.geneticmicro.com/ |
| Genometrix, Inc. | http://www.genometrix.com/ |
| Genomic Solutions | http://www.genomicsolutions.com/ |
| Imaging Research, Inc. | http://www.imagingresearch.com/ |
| Intelligent Automation | http://www.ias.com |
| Molecular Dynamics, Inc. | http://www.mdyn.com/arrays/arraywhat.htm |
| Radius Biosciences | http://www.ultranet.com/~radius |
| Research Genetics | http://www.resgen.com |
| ScanAlyze software | http://bronzino.stanford.edu/ScanAlyze/ |
| Telechem International, Inc. | http://www.wenet/~telechem/ |
| Western Technology Martketing | http://www.westerntechnology.com/ |

TABLE 1-continued

Informative web sites for DNA microarray technology

| DNA microarray technology web sites | URL |
|---|---|
| Robotics | |
| Galil | http://galilmc.com/ |
| Parker-Compumotor | http://www.compumotor.com/ |
| Parker-Daedal | http://www.daedalpositioning.com/ |

EXAMPLE 1
Digoxigenin Enzymatic Detection for Microarray Analysis of E-Box Binding Related Gene Expression.

Realizing the advantages and problems of cDNA microarrays for expression profiling, in this study a new approach was developed based on utilizing digoxigenin (DIG) to label target cDNA produced from gene-specific primers, with subsequent incubation with anti-digoxigenin antibody conjugated with alkaline phosphatase (AP), and colorimetric or chemiluminescent detection. A set of genes containing the E-box binding element (CACGTG), located in promoter regions of many genes, was selected as the probes. Probably the best-known representative of E-box-binding genes is c-Myc, whose transactivating activity plays crucial roles in the regulation of cell cycle, proliferation and apoptosis (Eilers, M. Mol. Cells 9, 1–6 (1999); Dang, C. V. Mol. Cell Biol. 19, 1–11 (1999); Facchini and Penn FASEB Journal 12,633–651 (1998)). Genes interacting with or regulating expression for c-Myc, as well as some target genes whose expression is E-box-binding-dependent, are included in this microarray. These custom-designed microarrays, combined with the enzymatic approach to label hybridization probes, allow the development of an inexpensive, user-friendly system for high-throughput gene screening assay of specific subgroups of gene expressions.

Materials and Methods
  Selection of Probes for Arraying
  E-box-binding proteins, as well as c-Myc-regulating, -interacting and target genes, were chosen from different data bases—GeneAtlas (http://www.citi2.fr/GENATLAS), GeneCards (http://bioinfo.weizmann.ac.il/cards), GenBank (http://www.ncbi.nkm.nih.gov/Web/Genbank) and PubMed (http://www.ncbi.nlm.nih.gov/PubMed). Unigene (http://www.ncbi.nlm.nih.gov/UniGene/index.html) cluster numbers and sequences were used to identify genes and verify their uniqueness. Nine housekeeping genes, as well as HeLa cell DNA were selected as positive controls; as negative controls, lambda DNA and 2× SSC (2× standard salt solution–0.3 M NaCl, 30 mM Na citrate, pH 7.0) were chosen. For each gene, a pair of primers was generated with the help of Primer3 software (Rosen and Skaletsky (1998) Primer3. Code available at http://www-genome.wi.mit.edu/genome_software/other/primer3.html). The program parameters were chosen in such a way that the melting temperature of the amplicon should be close to 80° C. but not more than 88° C. or less than 75° C., the length of the amplicon was to be generally around 450 bp (with a few outlyers between 300 and 700 bp), with primer annealing temperature about 60° C., and average length of primers 23 bp. Sequences of all amplicons have been carefully verified using proprietary software (BLASTN, FASTA), to avoid homology with repetitive elements and other related sequences, and also to distinguish between genes from the same family. A full list of all selected genes is represented in Table 1.

DNA, RNA and mRNA Isolation

Total RNA and DNA were isolated from approximately $10^8$ HeLa cell cultures and human peripheral lymphocytes isolated from fresh blood aliquots using Trizol reagent (Gibcio BRL, Burlington, ON). DNA and RNA concentrations and quality were determined by spectrophotometric and gel electrophoresis analysis in 0.8 or 2% agarose gels, respectively. Poly(A)$^+$RNA was isolated from 150 µg of total RNA using the Oligotex mRNA kit (Qiagen, Mississauga, ON), according to the manufacturer's instructions.

Amplification and Purification of Probes

10 µg of total RNA was reverse-transcribed in 40 µl reaction, using 200 U of MMLV (Gibco BRL, Burlington, ON) according to the manufacturer's instructions. Two PCR reactions for each pair of primers were conducted in a total volume of 100 µl, in a GeneAmp PCR system 9700 (PE Applied Biosystems, Norwalk, Conn.). Each 50 µl reaction (10 mM Tris-HCl, pH 8.6, 50 mM KCl, 0.1% Triton X-100, 1.5 mM MgCl$_2$, 0.5 mM of each dNTP, 20 pM of each primer, 1.25 U of Taq DNA polymerase (Amersham Pharmacia Biotech, Baie d'Urfe, QC) and 10 µl of RT reaction or 100 ng of genomic DNA) was thermal-cycled as follows: first cycle at 94° C. for 5 min, 35 cycles at 94° C. for 45 see, at 60° C. for 1 min and at 72° C. for 30 sec, the last cycle at 72° C. for 7 min. Probes that could not be amplified in RT-PCR were extracted from genomic DNA, with the condition that the primers were selected in the 3' region of a gene. Size and yield of PCR products were determined by gel electrophoresis in 2% agarose. Then PCR products were purified from solution or agarose gel bands, following preparative agarose gel electrophoresis (if by-products were determined), using GFX columns (Amersham Pharmacia Biotech, Baie d'Urfe, QC). After purification, concentrations of all probes were estimated by agarose gel electrophoresis, and adjusted to approximately 100 ng/µl.

Robotic Arraying

Purified PCR products in 2× standard salt solution (SSC) were arrayed in triplicates from 384-well plates, utilizing a GeneMachines™ OmniGrid microarrayer (Genomic Instrumentation Services, San Carlos, Calif.) equipped with Chip-Maker2 tips (Telechem International, San Jose, Calif.). The spacing between dots was 400 µm. The positions of genes in this array are indicated in Table 4. Microarrays were printed on Hybond-N or Hybond-N+ nylon membranes (Amersham Pharmacia Biotech, Baie d'Urfe, QC), attached to standard glass slides with tape. Before and after each 10 slides with membranes, regular slides were inserted to inspect printing quality. After arraying, membranes were UV irradiated at 50 mJ (GS Gene linker, Bio-Rad, Hercules, Calif.) to immobilize the DNA; then fragments of membranes containing arrays (approximately 1×1.5 cm) were cut off, denaturated in boiling water for 5 min, rinsed in 0.1% SDS for 5 min, and used for prehybridization. After the UV irradiation step, membranes can be stored attached to glass slides.

Preparation of DIG-labeled cDNA for Hybridization

An initial mix of gene-specific primers (GSP) was produced. For this purpose, 1 nM of each primer that was used in RT-PCR reactions to prepare probes was mixed in a total volume of 250 µl. Digoxigenin (DIG)-labeled targets were produced in RT reaction as follows: 1 µl of GSP, 4 µg of total RNA, and RNAse-free water in total volume of 14 µl were heated at 65° C. for 15 min to denature the RNA, and then kept at room temperature for 5 min for primer annealing. Alternatively, 2 µg of mRNA and 400 ng of oligo $(dT)_{12-18}$ primers were used. The reaction mix, containing 8 µl of 5× first strand buffer supplied by the enzyme's manufacturer, 2 µl of 10 mM mix of dATP, dCTP and dGTP (final concentration 500 µM each), 4 µl of 0.1 M DDT, 0.7 µl RNAguard, 31 U/µl (Amersham Pharmacia Biotech, Baie d'Urfe, QC), 10 µl of a 2 mM mix of 19:1 dTTP:DIG-11-dUTP (Roche, Laval, QC) and 2 µl (200 U/µl) of Moloney murine leukemia virus reverse transcriptase (MMLV RT) (Gibco BRL, Burlington, ON), was added. Reaction was carried out at 37° C. for 1 h, followed by enzyme degradation at 94° C. for 5 min in GeneAmp 9700. Alternatively, Omniscript reverse transcriptase (Qiagen, Mississauga, ON) was used according to the manufacturer's instructions. Labeling reactions were purified on GFX columns; this step eliminates all labeled products shorter than 100 bp, as well as unincorporated nucleotides, primers and protein.

After purification, efficacy of labeling was estimated as follows: 1 µl of 1:100, 1:1000, 1:10000 and 1:100000 dilutions were spotted on Hybond-N membrane, together with dilutions of control DIG-labeled DNA at known concentrations (10–0.01 pg/µl) as standardization for our assays (Roche, Laval, QC); after immobilization with UV, the membrane was incubated with alkaline phosphatase (AP)-conjugated antibody to DIG (Anti-DIG-AP), rinsed, and stained with chemiluminescent substrate, Disodium 3-(4-methoxyspiro{1,2-dioxetane-3,2'-(5'-chloro)tricyclo[3.3.1.1$^{3.7}$]decan}-4-yl) phenyl phosphate—CSPD (Roche, Laval, QC), according to the manufacturer's instructions.

Hybridization and Processing

For hybridization and pre-hybridization, DIG Easy Hyb buffer (Roche, Laval, QC), or formamide buffer containing 50% deionized formamide, 5× SSC, 2% blocking solution (Roche, Laval, QC), 0.1% N-lauroylsarcosine, 0.02% SDS, 100 µg/ml denaturated salmon DNA, were used. Membranes were pre-hybridized at 42° C. for 2 h in a hybridization oven (Autoblot, Bellco, Vineland, N.J.). Hybridization was performed at 42° C. overnight in 1 ml or less of hybridization solution, in 5-ml Falcon tubes. The concentration of labeled probes in the hybridization mix constituted 10 ng/ml. Before hybridization the probes were denaturated at 65° C. for 10 min in hybridization solution.

Afterwards, hybridization membranes were rinsed (unless mentioned specially) twice with 1× SSC, 0.1% SDS for 15 min at room temperature, and then with prewarmed 0.1× SSC, 0.1% SDS for 15 min at 68° C. Alternatively, membranes were rinsed in more stringent conditions, i.e. twice in 2× SSC, 0.1% SDS at 68° C. for 30 min, and twice in 0.1× SSC, 0.1% SDS at 68° C. for 30 min. After equilibration for 5 min in rinsing buffer (0.3% Tween 20 in maleic buffer (0.1 M maleic acid, 0.15 M NaCl, pH 7.5)), membranes were blocked for 1.5 h in 1% blocking solution under slight agitation, and then treated for 30 min in 10 ml of alkaline phosphatase-conjugated sheep anti-digoxigenin antibody (Roche, Laval, QC), diluted 1:1000 for colorimetric staining, or 1:10000 for chemiluminescent detection. Following antibody incubation, membranes were rinsed three times for 15 min in rinsing buffer, equilibrated for 2 min in detection buffer (0.1 M Tris-HCl, 0.15 M NaCl, pH 9.5), and stained with 175 µg/ml 5-Bromo-4-chloro-3-indolyl-phosphate, toluidine salt (BCIP), and 330 µg/ml Nitro blue tetrazolium chloride (NBT) in detection buffer. Alternatively, 1:100 dilution of CSPD was applied, and chemiluminescence was detected according to the manufacturer's recommendations (Roche, Laval, QC) using BioMax MR Kodak film.

Scanning and Evaluation of Arrays

Arrays were scanned on an Olympus microscope equipped with a Multiscan-4 System (Applied Scientific Instrumentation, Eugene, Oreg.) and a color CCD Sony 950 camera. Data acquisition and montage of different fields of view into one file were accomplished with the help of the Northern Eclipse Imaging System (EMPIX Imaging, Missisauga, ON). Quantitative measurements of intensity of enzymatic reaction at each dot, background subtraction, normalization to housekeeping genes, and comparison of paired hybridizations were all performed with an in-house software program.

Results

Selection of Probes and Primers

After careful evaluation of different data bases, 61 genes were selected for arraying, including 9 housekeeping genes. This set of genes contains 38 E-box binding genes, together with the Myc (c-, N-, L1 and L2) family, 5 c-Myc regulating factors (ZFP161, nm23-H2S, MBP-1, RBMS 1 and RBMS2), 5 c-Myc interacting genes (YY1, TFII-1, PAM, MM-1 and alpha-tubulin), and 4 c-Myc target genes (prothymosin alpha, MRDB, ODC1, and cdc25A). Positive controls include 9 housekeeping genes with different levels of expression (UBC, beta-actin, GADPH, HPRT1, phospholipase 2, HLA-C, PRS9, aldolase C, and RPL13A), and also HeLa genomic DNA. Lambda DNA and 2× SSC (2× standard salt solution), which was used as solvent for all probes, were selected as negative controls.

Primers for all genes were selected with the help of Primer3 software, provided that they corresponded to the same conditions for PCR reaction, and produced products of similar melting temperature. Most products were produced from HeLa or lymphocyte cDNA. In case PCR amplification failed from cDNA, primers were selected in 3' region of these genes, and amplicons were produced from HeLa genomic DNA. The average annealing temperature of primers was 60.1±0.9° C., which allowed all PCR reactions to be in the 96-well format. Sizes and melting temperatures of products, and annealing temperatures of primers, are represented in Table 4. The average size of PCR products for arraying, and their melting temperature, were 441±58 bp and 80±3° C., respectively. Selecting these parameters allowed hybridization and post-hybridization rinsing in stringent conditions, decreasing drastically the possibility of cross-hybridization and background level.

Scrupulous selection of primers could be used to distinguish in some cases between very close members of gene families (for example, USF1 and 2, ID2, 3 and 4, members of the Myc family, and so on), or between two different transcripts of c-Myc. As is well known, there are several different transcription forms of c-Myc, transcribed from different promoters, with varying regulation properties (Bodescot and Brison Gene 174, 115–120 (1996)). Selecting primers in the $1^{st}$ exon and the $2^{nd}$-$3^{rd}$ exons allowed discrimination between full-size and truncated forms of c-Myc.

Conditions Influencing Hybridization

Several parameters which probably influence the results of hybridization with cDNA microarrays printed on nylon membranes were carefully tested. First of all, gene profiling results were examined using either mRNA or total HeLa RNA. Surprisingly, the whole pattern of expression was very similar, with the exception of a few genes (UBC, RPL-13A, MBP-1) the signals from mRNA were several times higher; the most prominent difference was found in UBC, where it approached 5-fold. Alternatively, signals for HPRT 1 and phospholipase A2 were higher with total RNA. In conditions where quantity of mRNA is a limiting factor, total RNA can be used instead, without significant differences in results of expression profiling.

Comparison of two reverse transcription enzymes, Moloney murine leukemia virus (MMLV) (Gibco BRL, Burlington, ON) and OmniScript (Qiagen, Mississauga, ON), used for production of digoxigenin-labeled targets for hybridization, did not reveal any difference in expression profile when gene-specific primers were used; but signal intensity was stronger after labeling with MMLV, especially after a day of staining (Table 5). When oligo(dT) primers were used with mRNA, some significant differences in expression levels of several genes were detected. Labeling with OmniScript produced 2–3 times more intense signals for RP-S9, RP-L13A, enolasel, N-Myc and MAD4.

To decide which buffer is better for hybridization with microarrays, we compared EasyHyb (Roche, Laval, QC) and formamide-based buffers. The expression profile of HeLa mRNA was found to be independent of buffer composition, but signals were higher after hybridization in formamide buffer (Table 2), and addition of 2% blocking reagent further reduced background in comparison with EasyHyb, thereby facilitating subsequent scanning and image evaluation.

No substantial differences were found in expression profile of HeLa mRNA when rinsing conditions of different stringency were used (see Materials and Methods). More stringent rinsing evenly lowered all signals, and produced signals with sharper borders, rendering them easier to scan and evaluate. Standard rinsing conditions are probably already stringent enough in hybridizations with cDNA microarrays and gene-specific primers; therefore standard rinsing is preferred, because it is not so time-consuming.

Comparison of positively charged (Hybond-N+) with neutral (Hybond-N) nylon membranes revealed no differences in sensitivity. Aside from this consideration, the neutral (Hybond-N) nylon membrane is preferable due to its stronger texture for printing support. This strength was not found in the positively charged Hybond-N+ membrane, which was found to retain visible printing footprints, causing complications in image analysis and increased background.

As may be seen from Table 5, increasing the staining time from overnight to 1 day usually increased the overall strength of signals by only 10%. Longer staining time increased the background level of the reaction, which compromised the possible advantage of higher sensitivity. Variations in hybridization conditions can increase overall signal intensity by 30–40%. However, the positive effects are not additive, and the maximum difference in total intensity of microarrays approaches only 50%. The following conditions for hybridization of DIG-labeled targets with the cDNA microarray are optimal: printing probes on neutral nylon membrane, reverse transcription reaction with total RNA, gene-specific primers and MMLV reverse transcriptase, hybridization in formamide buffer, and standard rinsing conditions. These conditions were implemented in the experiments described in the following paragraphs.

Specificity, Sensitivity and Reproducibility of Hybridization

To evaluate the specificity of cDNA microarray hybridization, 5 genes (MRDB, ODC, TFII-1, cdc25A and c-Myc), covering the entire range of length (368–711 bp) of arrayed products, were labeled in multiplex PCR reaction and hybridized with cDNA arrays. As expected, only 5 samples on the array were positive, as well as the HeLa genomic DNA as control since it will hybridize with the locus where HeLa genomic DNA was spotted at the highest concentration at the position 51, and negative show little or no detection at the positions 1a and 1b where spotted HeLa genomic DNA is of low quantity. In all, these experiments demonstrate no signs of cross-hybridization (FIG. 3).

Figure 4:
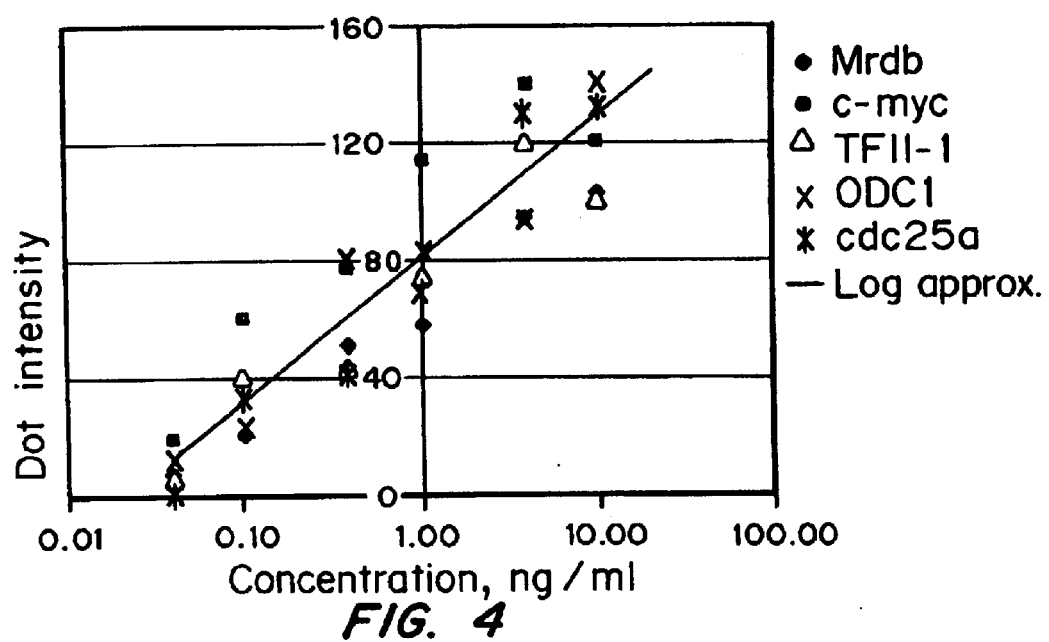
FIG. 4 shows the relationship between concentrations of 5 genes including Mrdb, c-Myc, TFII-1, ODC1, and cdc25a, and intensity of hybridization signals. Logarithmic approximation is shown. Dot intensity is represented by the arbitrary units on the Y-axis; concentration is measured as ng/ml on the X-axis.
Figure 5A:
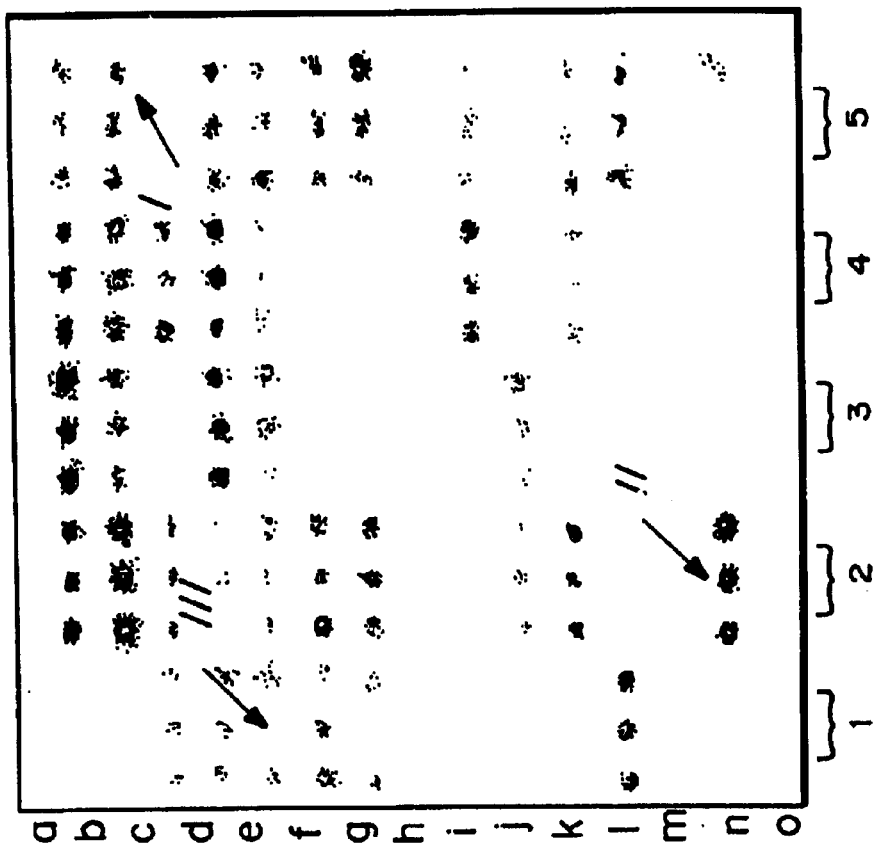
FIGS. 5A and 5B show the expression profiles of E-box-related genes in Hela cells (FIG. 5A), and normal human lymphocytes (FIG. 5). Arrows within the matrix show positions of: I—Aldolase C; II—Mad4; III—MBP-1.
Figure 5B:
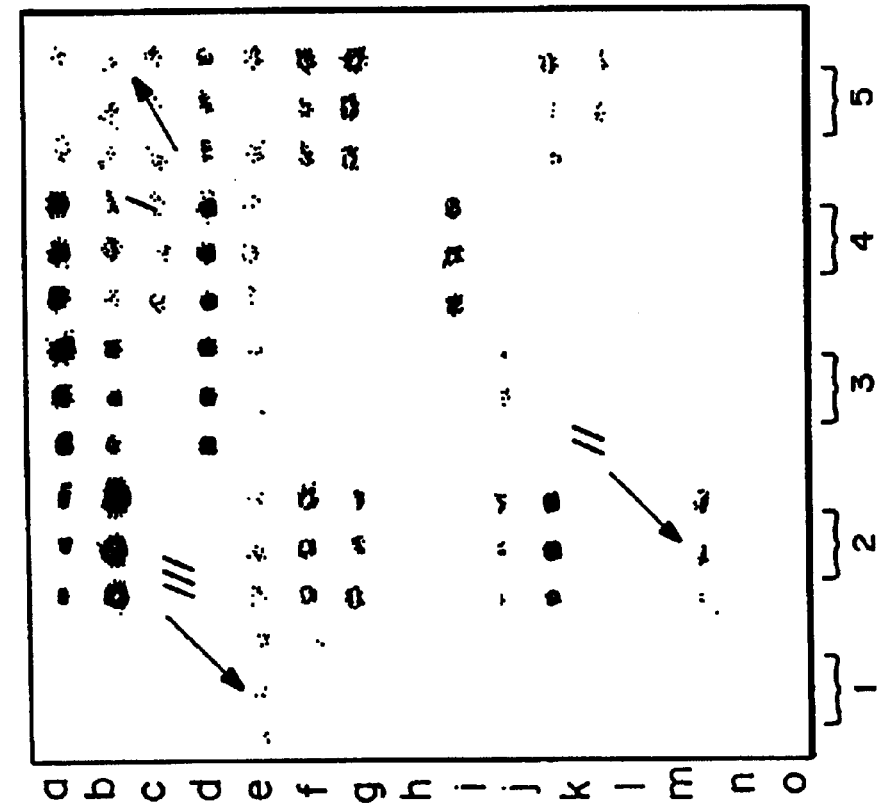

To estimate the sensitivity and derive a calibration curve for cDNA microarray hybridization, different concentrations of this 5-gene PCR mix (10, 4, 1, 0.4, 0.1 and 0.04 ng/ml) were hybridized with arrays. The results of this experiment are presented in FIG. 4. Linear dependence in semi-logarithmic coordinates, with an obvious plateau in the region of 4–10 ng/ml, was observed for all genes, with the same slope of 45±2. The lower limit of detection varies slightly for different probes in the array, and corresponds to 40–100 pg/ml per individual gene. These results are close to the detection limit of the digoxigenin system (10–30 pg/ml), according to the manufacturer (Roche, Laval, QC). This level of sensitivity allows detection of mRNAs of intermediate abundance, each representing more than 0.04% of total cell mRNA. Taking into account this detection level, it is estimated that for hybridization with a microarray containing about 70 genes of intermediate abundance, 7 ng of labeled probe produced from gene-specific primers should suffice. For the next hybridizations, a concentration of labeled probes of 10 ng/ml was selected. The yield of standard reverse transcription labeling reaction with gene specific primers is about 20–40 ng; therefore, one labeling reaction yields enough product for 2–4 independent hybridization reactions. In contrast to unstable radioactive probes, DIG-labeled probes can be stored and reused several times. Reusing hybridization mixes 2–3 times, after storing at −20° C. for several months, gave results quite concordant with the original ones.

The arrays were scanned at a resolution of 3600 dpi, and results were compared with results of microscope scanning. In general, variability between replicated dots was higher in the case of the scanner, and linearity may be influenced by the scanner's software. The scanner can be used for initial evaluation of hybridization results, especially when chemiluminescence detection is implemented.

Expression Profiling of Hela Cells in Comparison with Human Lymphocytes

Expression profiles of E-box genes were determined in replicating HeLa cells and normal human lymphocytes. In lymphocytes, the most prominent alteration consisted of more than 2-fold up-regulation of E-box-related genes TCF4, MAD4 and Aldolase C. Alternatively, down-regulation of c-Myc-regulating genes MBP1 and Nm23-H2S, and small down-regulation of c-Myc and up-regulation of N-Myc, were registered in lymphocytes in comparison with HeLa cells. Expression of some c-Myc interacting and target genes was down-(MM-1, ODC1) or up-regulated (PAM, MrDb) in lymphocytes. Also, small up-(MITF, ID2) and down-(TFEB) regulation was detected in expression of several E-box-binding genes in lymphocytes, in comparison with HeLa cells.

Summary cDNA and oligonucleotide microarrays are becoming an increasingly powerful technique for investigating gene expression patterns. In spite of the fast progress in this field, some limitations of the technique persist. One of the major obstacles is the requirement for a large amount of mRNA. Another problem with existing microarray systems is data mining; while information on expression of tens of thousands genes is absolutely vital to estimate the functions of new genes, in some instances a researcher is interested in the expression profile of only a subset of genes, in many physiological conditions. The significant differences in expression of 3–6 genes out of 61 are already much more manageable than can be detected from ordinary microarrays with massive numbers of genes, in the hundreds or thousands. For example, in SAGA analysis of 45,000 genes, it was found that about only 1% are differentially expressed in normal and cancerous human cells. A similar estimation resulted from analysis of expression profiles in young and old mice; expressions of only 1.8% of about 6,000 genes are changed more than 2-fold.

Printing microarrays on nylon filters, and using digoxigenin to label the cDNA with gene-specific primers, permits use of as little as 4 µg of total RNA per hybridization. This is the same sensitivity that can be attained with radioactivity in the Clontech protocol, and it is much more sensitive than ordinary microarrays, which need several µg of mRNA. In addition, DIG-labeled probes of high labeling sensitivity can be stored for a long time, and reused several times, in contrast to fluorescently or radioactively labeled ones.

Proprietary selection of genes for inclusion in a microarray, and using digoxigenin for labeling, also helps avoid another disadvantage of radioactive labeling: genes in the E-box microarray are all in the same category of abundance (intermediate or low abundant). Excluding highly abundant genes eliminates the problem of merging of strong signals. Merged signals in some circumstances substantially complicate the process of scanning, and create unreliable results during the data acquisition step.

I claim:

1. An improved method of detecting changes in the expression of genes in a microarray, wherein the genes comprise an E-box regulatory sequence, or encode proteins or cofactors that bind to the E-box regulatory sequence, the improvement comprising
   a) providing a set of primers for reacting with a nucleic acid sequence in the genes in the microarray, with the sequence having a length of between 480 and 700 base pairs and a inciting point of between 75 and 85° C., and comprising a non-consensus sequence so that there is no detectable hybridization with homologous Sequences;
   b) reacting the set of primers with the genes to amplify the nucleic acid sequence to form amplicons;
   c) arraying the amplicons produced for the reaction in step (b) onto a solid support; and
   d) reacting the amplicons with a labeled probe comprising all or a portion of the non-consensus sequence; and
   e) detecting levels of hybridization between the amplicons and the labeled probe, thereby detecting levels of gene expression; and comparing the gene expression to the expression of control genes, thereby detecting any changes in expression levels.

2. The method of claim 1 for screening for differential expression of one or more E-box regulatory genes or genes interacting with genes binding to the E-box regulatory sequence, comprising:
   a) providing a first library of genes associated with a particular disease, disorder or state,
   b) providing a second library of genes, obtained from cells having a different state, disease, or disorder to a compound to be tested;
   c) detecting or measuring expression of selected genes in the flint and second library using the method of claim 1,
   d) comparing the expression of the selected genes in the tint and second libraries, and
   e) detecting which genes have altered expression in the second library.

3. The method of claim 2 wherein the state is selected from the group consisting of age, cancer and diseases or disorders of the cardiovascular, neurological, and musculoskeletal systems.

4. The method of claim 2 wherein the compound is a drug or toxin.

5. The method of claim 2 further comprising normalizing results of expression by comparison with levels of expression of housekeeping genes.

6. The method of claim 1 for determining the effect of a compound on the disease or state of an individual comprising:
   a) providing a DNA library, including genes comprising an E-box regulatory sequence or encoding proteins or cofactors that bind to the E-box regulatory sequence, wherein the genes me obtained from the individual after treatment of the individual, or cells or tissues derived therefrom, to the compound or a particular dosage regime of the compound,
   b) screening the library for changes in levels of expression of the selected genes using the method of claim 1, and
   c) correlating the changes in expression with the state, disease or disorder prior to treatment.

7. The method of claim 6 wherein the cells or tissues are treated with one or more compounds in vitro prior to making the DNA library.

8. The method of claim 6 wherein the compound is selected from group consisting of proteins or peptides, sugars or polysaccharides, nucleic acid molecules, and synthetic molecules.

9. The method of claim 6 wherein the library is derived from cells obtained from an individual of a particular age, having a particular disease or disorder, or derived from the neurological system, the cardiovascular system, the musculoskeletal system, or cancerous tissues.

* * * * *